(12) United States Patent
Synder

(10) Patent No.: US 8,133,127 B1
(45) Date of Patent: Mar. 13, 2012

(54) SPORTS TRAINING DEVICE AND METHODS OF USE

(76) Inventor: Terrance W. Synder, Trappe, PA (US)

(*) Notice: Subject to any disclaimer, the term of this patent is extended or adjusted under 35 U.S.C. 154(b) by 0 days.

(21) Appl. No.: 12/460,580

(22) Filed: Jul. 20, 2009

Related U.S. Application Data

(60) Provisional application No. 61/135,495, filed on Jul. 21, 2008.

(51) Int. Cl.
*A63B 69/36* (2006.01)
(52) U.S. Cl. ........................................ 473/274; 473/257
(58) Field of Classification Search .................. 473/207, 473/208, 211, 257, 266, 269, 274, 275, 409
See application file for complete search history.

(56) References Cited

U.S. PATENT DOCUMENTS

| | | | | | |
|---|---|---|---|---|---|
| 3,325,169 | A | * | 6/1967 | MacKniesh | 473/140 |
| 3,415,523 | A | * | 12/1968 | Boldt | 473/209 |
| 3,770,280 | A | * | 11/1973 | Straus | 473/209 |
| 4,521,023 | A | * | 6/1985 | Williams | 473/274 |
| 5,439,226 | A | * | 8/1995 | Luedtke | 473/232 |
| 5,577,729 | A | * | 11/1996 | Sabour | 473/274 |
| 5,634,858 | A | * | 6/1997 | Bellagamba | 473/257 |

* cited by examiner

*Primary Examiner* — Nini Legesse
(74) *Attorney, Agent, or Firm* — Law Office of Jeffrey R. Ramberg

(57) ABSTRACT

The various embodiments of the present invention include, but are not limited to, sports training devices that are beneficial for training in activities requiring swinging motions (e.g., the game of golf). The device may be used without hindering any portions of a natural swing. The invention also contemplates continuous tactile feedback to the user, and is both foldable and transportable, while also being economical.

2 Claims, 4 Drawing Sheets

SPORTS TRAINING DEVICE AND METHODS OF USE

CROSS-REFERENCE TO RELATED APPLICATIONS

This patent document claims the benefit of the filing date of U.S. Provisional Patent Application No. 61/135,495, filed on Jul. 21, 2008, in the name of Terrance W. Snyder. The entire contents of this related patent application are herein expressly incorporated by reference.

STATEMENT REGARDING FEDERALLY SPONSORED SUPPORT (none)

BACKGROUND OF THE INVENTION

The invention generally relates to training of repetitive body motions, more specifically relating to sports requiring swinging movements (e.g., golf). The invention more particularly concerns a device that trains the body, and in-particular, the head, to create repeatable motions of proper form.

Sporting events—particularly golf—require swinging movements which are very repeatable and of good technique, to achieve a skill level to play competitive or even casual golf. Professional and amateur golfers will agree that it is a difficult game to master, but learning certain movements and being able to repeat them will set the ball in good motion. God given talents, such as good hand-eye coordination, help these efforts; however, most of the learning process regards physical movements which must all be performed in concert. That is, the position of the body must coordinate with the timing of the swing, and the plane of the actual swing must coordinate with the natural rotation of the body, and the placement of the ball.

The swing plane is a plane through which the club is swung, and the proper swing plane travels through the position of the head; additionally, the head is at the center of the ideal swing plane. Indeed, the coach of a famous golfer was once noted as having grabbed the hair of his student, while the swing was practiced, so as to keep the head stationary. Movement of the head will cause varying angles of contact, when the club actually strikes the ball, thereby affecting shot consistency.

Many training aids have been developed to address the myriad aspects of the perfect golf swing. However, these existing devices leave much to be desired.

One such device uses elastic bands to position the arm relative to the hip during the swing. See, for example, U.S. Pat. Nos. 6,027,413, and 6,672,115. A similar device uses a harness around the user's chest. See U.S. Pat. No. 5,586,761. Yet another device uses a combination of a hip and chest attachment. See U.S. Pat. No. 5,050,885. These devices are restrictive regarding certain aspects of the golf swing; additionally, they appear cumbersome and/or expensive, and may actually interfere with other aspects of a proper swing. Practicing a swing with a harness or chest-attachment is likely to—in itself—lead to a faulty swing, when the devices are removed.

Devices exist that are designed to show the axis of rotation or swing path, these generally use lights, infra-red detectors, or LASER beams to track the movement. See, for example U.S. Pat. Nos. 6,071,202, 5,087,047 and 6,059,668, respectively. These devices require complicated electronics, and are difficult to actually set-up and use.

Another approach to limiting body movement, is to brace the lower leg region. See, for example, U.S. Pat. No. 6,024,656. These leg braces may inhibit unwanted movement, but they also prohibit the natural weight shifting, from one leg to another, and the natural twisting of the upper and lower torso during the swing itself; and especially during the follow-through. A similar approach may be seen taken with positioning posts or standard crossbars. See U.S. Pat. No. 5,303,926. These may be employed near the body of the golfer to prevent swaying of the torso, however, this device suffers the same limitations as the predecessor device. Additionally, if it is moved out of the way of the swing, and the natural movement of the torso during a proper swing, it will not be visible. Moreover, if sight-checking to orient the golfer during the swing is the mechanism of operation—in any of these devices—the golfer will be distracted from one of his or her primary goals; that is, keeping the eye on the ball.

Devices do exist which are designed to monitor the movement of the head. One such device can be seen in U.S. Pat. No. 6,941,779, where gyroscopes are used to monitor the head's movement. Additionally, gyroscopes monitor the attitude of the head. See U.S. Pat. No. 6,911,635. However, these types of devices measure rotation of the head, and can not measure minor or discrete linear movement. Of course, all of those types of movement—not simply rotation—are important swing aspects to be monitored.

Another problem with gyroscopes is that they usually are only effective in a two-dimensional plane, see, for example U.S. Pat. No. 6,048,324, and therefore require a plurality to be connected serially to cover complete ranges of movement. As discussed previously, linear movement is easily detected by these gyroscopic arrays, and they therefore can not adequately assess angularity of a stance or how much a body part (e.g., head) lift or drop during any activity. Additionally, electronic devices of the sort detailed in the '324 patent need to be set or oriented between each use, which is hardly practical during the repetitive movements of swing practice.

Certain devices exist to measure linear movement, but this is accomplished by the measurement of acceleration. See, for example, U.S. Pat. No. 5,984,796. As such, slow movements with minimal acceleration may go undetected, while rapid minor movements will trigger an alarm. Minor movements, regardless of the speed or acceleration, may not be problematic to the swing itself, and would be detected, and or trigger an alarm.

Many of these aforementioned devices use audible alarm systems to alert the user of an unsatisfactory condition. While already focusing on the myriad swing principles, the addition of an audible alarm—midswing—can hardly be of help. Rather this type of feedback would perhaps detract from the aspects of the swing that were being performed correctly. It must be remembered that the casual golfer, as well as the professional, can only assimilate information as fast as the brain can process it.

Additionally, each of these devices focuses on single aspects of the swing, so many devices would be required. This is both expensive, and difficult to store and/or transport for practice.

SUMMARY OF THE INVENTION

The various embodiments of the present invention overcome the shortcomings of the prior art. For example, among other things, the present invention contemplates a device that provides constant tactile feedback regarding body position (more specifically, head position) during a sporting activity (e.g., golf), while allowing full body movement (e.g., a golf swing).

In one embodiment, the device basically comprises a base; a vertical extension, which is adjustable as to height; a crossbar, which is adjustable as to length; and a signaling assembly. Additionally, the crossbar may be slidably attached to said vertical extension with an attachment device which affords adjustable compound movement.

In another embodiment the signaling assembly comprises a non-moving section which is arranged to contact the crown region of a person's head, during the golf swing. Alternatively, the signaling assembly comprises a head-piece which is rotatable about an axis (e.g., the axis of the crossbar).

In various of these embodiments, the signaling assembly is arranged, at the time of use, to gently contact the users head. The pressure is slight, but constant, during the user's motion (e.g., a golf swing). The constant pressure allows the user to concentrate on the myriad other attributes (e.g., proper weight transfer, keeping left arm straight, etc.), without having to react to an alarm or other intermittent signal. In actuality, the forward swing occurs rapidly, and reaction time would not allow the user to correct the improper movement until the next swing; whereas the current invention allows constant tactile feedback, which is easier for the brain to process. Additionally, the feedback of the present invention is analog; that is, the user can feel the pressure growing, and remedy the situation by slight adjustments, as opposed to the alarm devices that only signal when the swing has gone beyond an acceptable position or path.

Additionally, these various embodiments of the present invention allow the tracking of head movement in three dimensions. That is, the signaling assembly will resist or signal movement in the vertical, forward, and side-to-side directions.

A shock-absorbing or spring-like member may be attached between the signaling assembly and its mount, such that the signal to the golfer may begin more slowly, than if the signaling device were affixed in a more rigid fashion.

In yet another embodiment, the base and vertical extension may be replaced with a crossbar attachment, arranged such that said crossbar may be attached directly to a wall, or other stationary object.

In still yet another embodiment, a training device comprises a device for providing continuous feedback during a golf swing, wherein the device includes but is not limited to, a base, a vertical extension, and a crossbar, wherein said base is arranged to hold said vertical extension in an upright position, and said vertical extension may arranged to adjustably hold said crossbar in a specific orientation. The crossbar may incorporate a signaling assembly, which may be arranged to contact the head of the user, and may provide feedback when the user's head moves away from a predetermined location. The signaling assembly may further incorporate a spring or spring-like means or mechanism, which may serve to provide increasing amounts of feedback (e.g., tactile feedback, or audible feedback) as the device is used (e.g., during the swing of a golf club, or other sports device). The various elements of the device may be attached by split-body sections, which may serve to allow adjustment of heights and orientations (e.g., angles, and telescoping abilities). This device may also be arranged to be collapsible, which may serve to adjust the device, and stow it out-of-the-way when not in use, or it may serve to make it less obtrusive in its then-existing location.

In these various embodiments, it is envisioned that the device, whether utilizing a base and vertical extension, or a crossbar attachment, could be arranged to be foldable; thereby allowing for easier transport and storage. In the embodiment using the crossbar attachment configuration, it is contemplated that the device will stay at least semi-permanently affixed to a stationary object, and the folding aspect is simply to allow the device to be folded back out of the way.

DETAILED DESCRIPTION OF EMBODIMENTS OF THE INVENTION

A first embodiment of the present invention basically comprises a base, a vertical extension, a crossbar, and a signaling assembly, as will be described below.

Figure 1:
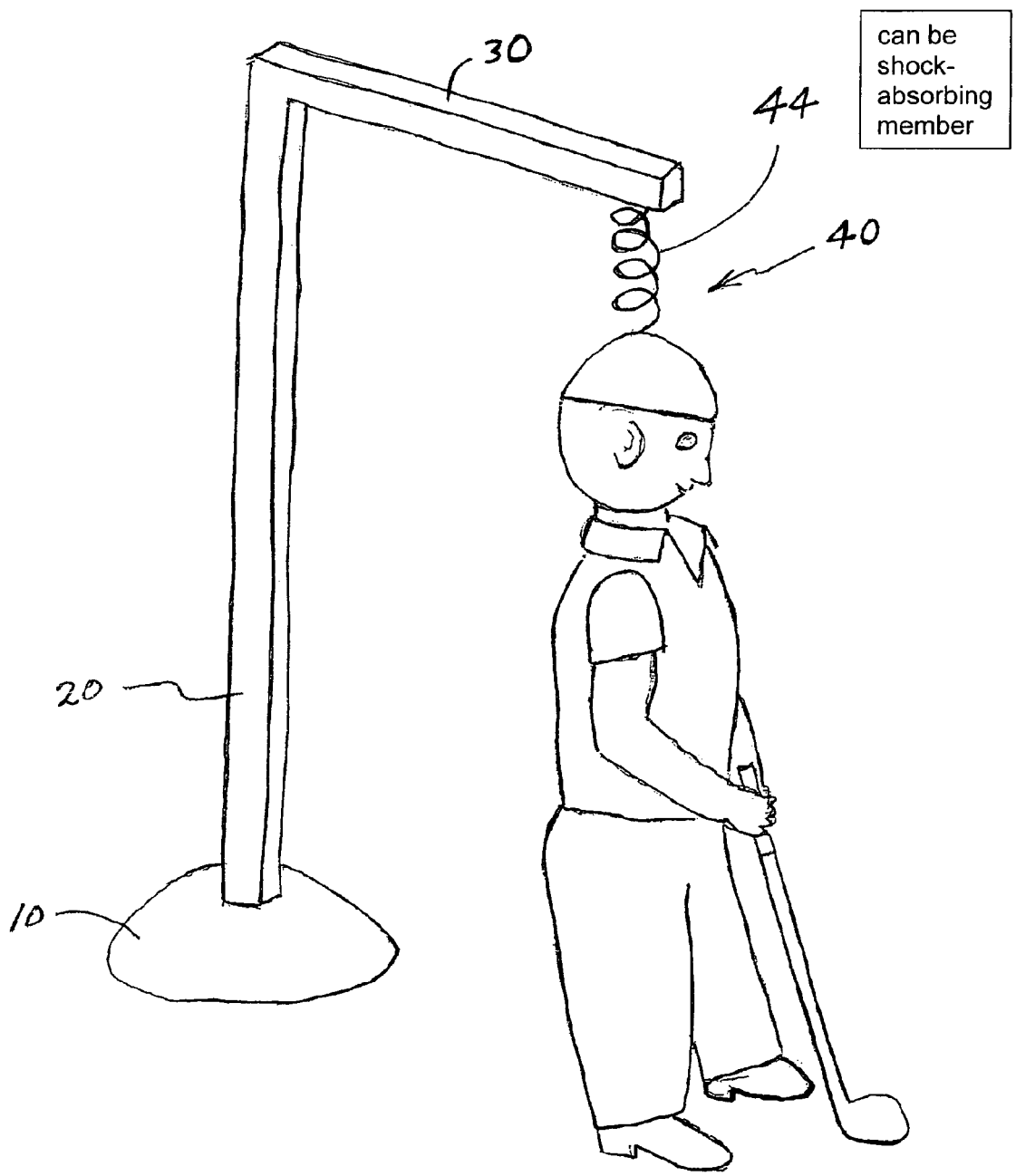
FIG. 1 shows an isometric view of an embodiment of the present invention, utilizing a base and vertical extension members.

The base 10, as shown in FIG. 1, basically holds the device stationary, and may be made of various materials and methods known to those skilled in the art. The base may be circular in footprint, or may be constructed of a tripod arrangement (not shown). The vertical extension 20 simply serves to hold the crossbar 30 at the appropriate height from the base 10. The crossbar 30 serves to hold the signaling assembly 40 at the correct position relative to the vertical extension 20. Thus, the signaling assembly 40 is positioned at the correct point in three dimensional space via the base 10, vertical extension 20, and the crossbar 30.

Figure 2:
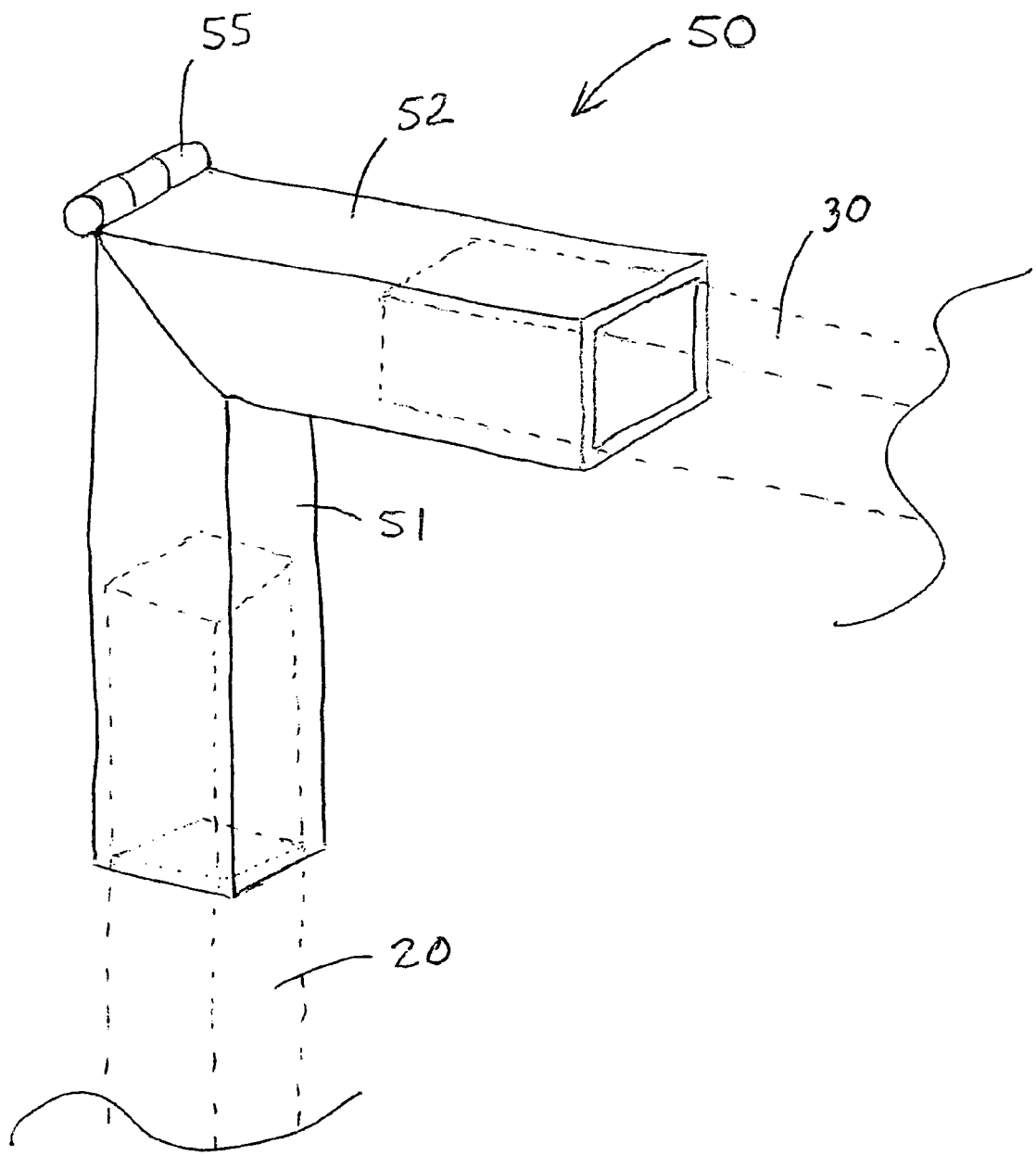
FIG. 2 shows a close-up isometric view of the attachment device.

The positioning of these elements may be made simple, yet variable by the use of compound adjustment. FIG. 2 shows an attachment device 50 which affords this device such compound adjustment capabilities. The crossbar 30 is slidably attached to said vertical extension 20, through a horizontal sleeve 52; likewise, the vertical extension 20 is slidably attached to said crossbar 30, through a vertical sleeve 51. Said sleeves are connected through a body 55. Rotational movement, of the crossbar 30 relative to the vertical extension 20, may be achieved by splitting the body 55 to allow the halves to rotate and to be fixedly attached to each other (not shown).

These movable elements may be secured in the desired position with attachments such as, but not limited to, wing nuts or Velcro™ hook-and-loop fabric, or other attachment methods known in the art. By way of example, the crossbar 30 may be moved to the desired height on the vertical extension, where the attachment device 50 may be used to fixedly secure the members.

In one embodiment, the crossbar 30 will be placed such that the signaling assembly 40 (to be described later) is in a position to gently contact the golfer's head, when the golfer is standing in the ideal posture. The vertical attachment 53 and the horizontal attachment 54, in the vertical sleeve 51 and the horizontal sleeve 52, respectively, may then be tightened to assure that the signaling assembly 40 will not move.

It is recognized that both the horizontal sleeve 52 and the vertical sleeve 51 need not be adjusted for each height of golfer; that is, the vertical sleeve 51, may be adjusted along the length of the vertical extension 20, without elongating or shortening of the length along the crossbar 30 being necessary. However, shortening in both directions (i.e., along the crossbar 30 and the vertical extension 20 may be desirable for easy transporting and storage.

Additionally, in an embodiment, the vertical extension 20, may comprise a telescoping member (not shown), wherein the vertical extension may be collapsed further into its base. These telescoping members may be made by the methods known to those skilled in the art, and suffice it to say that for example, the base may comprise a larger outside diameter, than the upper portion; and there should exist means to slidably attach each member.

The crossbar 30 of this invention, may be made to telescope similarly to the vertical extension 20, for the same reasons.

These various embodiments have shown methods through which the device may be constructed, such that the signaling assembly 40 may rest on top of the head of a short golfer through the tallest golfer. Also, the signaling assembly 40 may be oriented near to, or far from, the vertical extension 20. Thus, a golfer of any size may use the various embodiments described herein, and use a full and natural swing, just as is required on the course.

Figure 3:
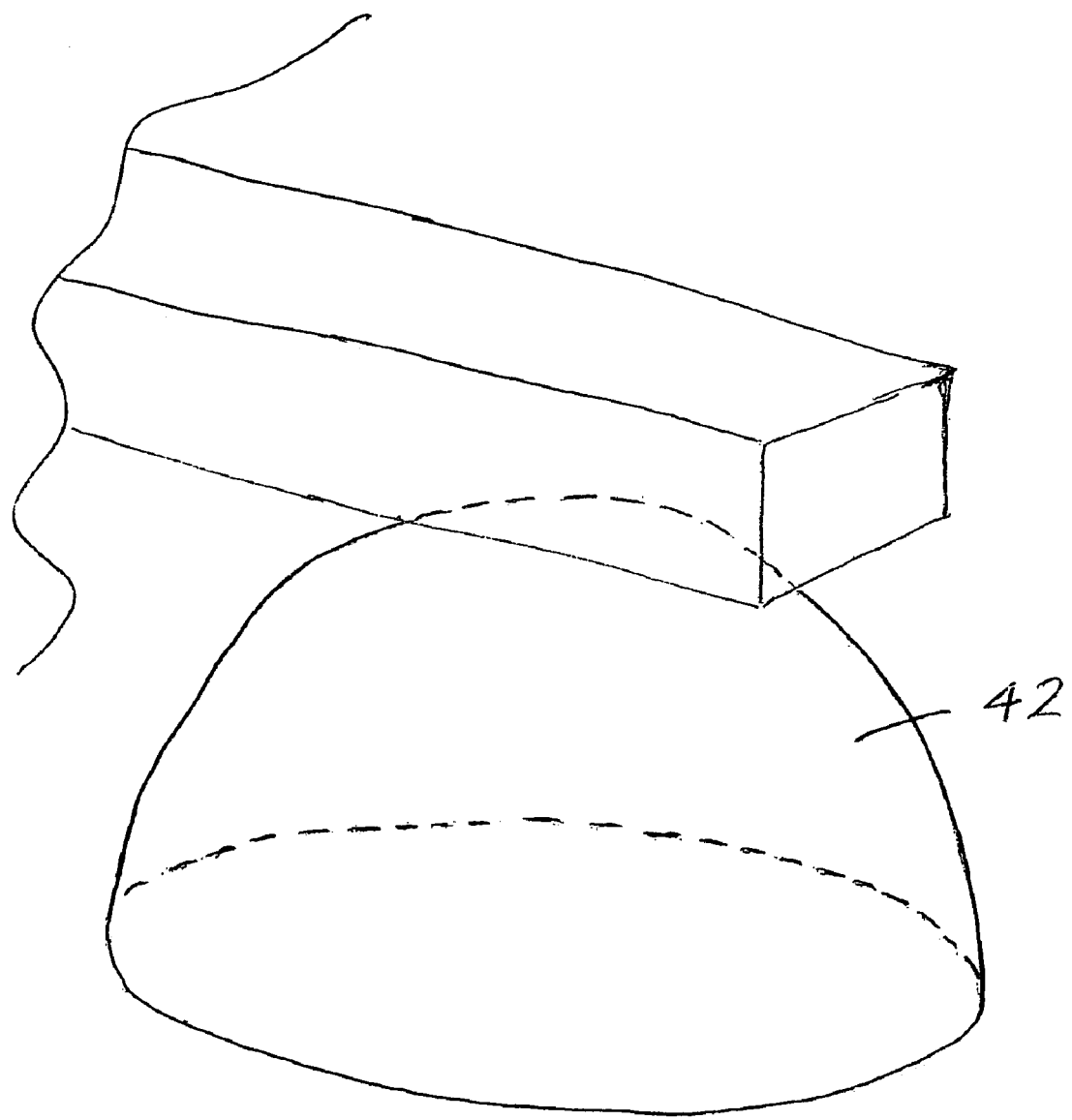
FIG. 3 shows a close-up isometric view of the signaling assembly.

The signaling assembly 40 may be of any design that enables the signaling of the head's position before, during and immediately following the swing. In one embodiment, the signaling assembly 40 simply comprises a dome-shaped cap 42 (i.e., a partial hemisphere) which would rest against the head (e.g., see FIG. 3). This arrangement would allow the signaling of movement of the head in three dimensions. That is, toward/away from the axis of the vertical extension 20, toward/away from the axis of the crossbar 30 (to the golfer's left or right side), and toward/away from the axis of the vertical extension in an upward/downward direction.

An embodiment of the signaling assembly 40 additionally comprises a spring mechanism 44 (shown in FIG. 1) or other suitable member that has elastic properties. This would allow for a signal to be transferred in a more comfortable fashion, that is, the head would come into gentle contact with signaling assembly 40. This could also ease the impact if the head were to leave contact, during the swing, and then rapidly regain contact.

This disclosure contemplates the use of a section of "artificial" turf, which may allow repeatable and predictable surfaces for the golf ball to rest on. Varying grass conditions may affect the swing, so removing this variable may better train the beginning golfer. Experienced golfers may hit from the natural grass, or use an artificial surface to avoid taking an excessive amount of divots during a practice session. Additionally, any artificial turf used with the embodiments of this invention may also comprise a "tee," similar to those commonly seen at practice ranges.

Figure 4:
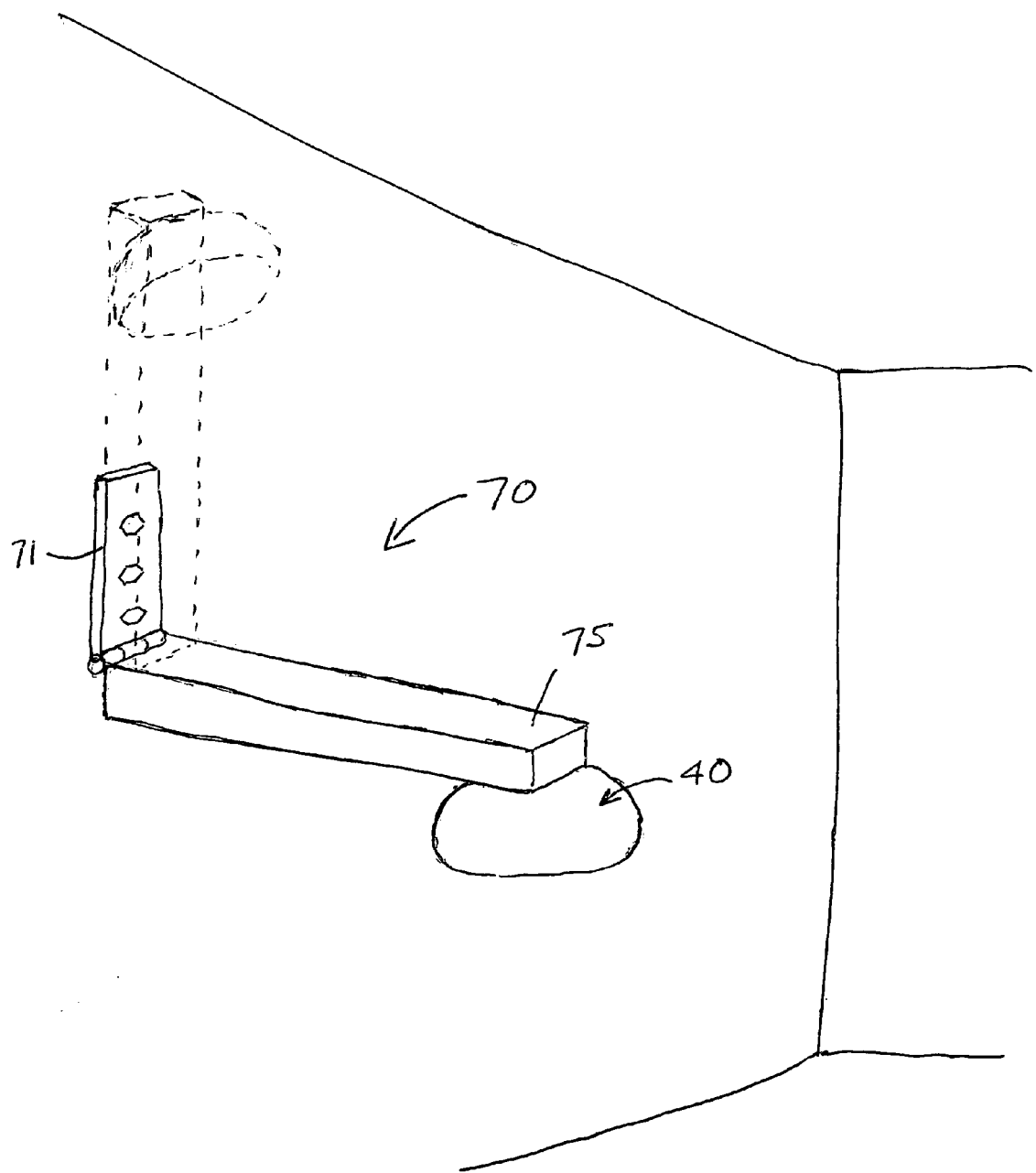
FIG. 4 shows an isometric view of a collapsible model embodiment of the present invention.

A fully "collapsible" or "stowable" embodiment is also envisioned, see, e.g., FIG. 4. This stowable embodiment 70 basically comprises a modified crossbar 75, and a signaling assembly 40. The signaling device may be similar to that previously disclosed, however the modified crossbar 75 performs functions not previously disclosed.

The modified crossbar 75 is arranged to connect to a wall or other permanent, or semi-permanent construct, whereby the modified crossbar 75 and signaling assembly 40 would be pulled from a "stowed" position (indicated by dashed lines) to a locked position (solid lines), where the device may be used. The device may be made moveable or rotatable by the use of a hinge 71 (or similar swiveling component) and "locked" into this position by a hinge-stop (not shown) where gravity acts to secure the device against the limiting stop, or the device may be locked in place by a latch, pin, or other securement means known in the art (not shown). Following such use, the locking means (if any) could be disengaged, and the device may be moved or swiveled to its "stowed" position. Once stowed, a second locking mechanism may be employed to again secure it. This would be enabled, in a preferred embodiment, by a backing plate (not shown), or by a simple hinge mechanism. A scissoring mechanism may also be employed (not shown), or other attachment means known to those skilled in the art.

While the various embodiments of this disclosure may be made of strong and durable weather-resistant materials (e.g., aluminum), the preferred material may be a less costly, and lighter weight material (e.g., PVC, etc.). The benefits of low weight may make a preferred embodiment more marketable as a transportable device, and a different market segment may prefer aluminum, for example, a collapsible model may better utilize the strength and durability of aluminum, since this model does not have to be transported.

It is envisioned that the most economic models may comprise vertical extensions and crossbars made from commodity PVC tubing; but higher strength materials may also be used. Additionally, the tubing may be of round cross-section, or it may be of triangular or other shape, which may ease manufacture and increase strength.

Thus, since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

What is claimed is:

1. A training device for providing continuous feedback during a golf swing, said device consisting essentially of a head movement signaling device comprising a base, a vertical extension, and a crossbar, wherein said base is arranged to hold said vertical extension in an upright position, and said vertical extension is arranged to hold said crossbar in a nearly horizontal orientation, wherein such crossbar comprises a signaling assembly, with said signaling assembly being arranged to contact the head of the user of said device, thereby giving said feedback when, the head begins to move away from a predetermined location, and wherein said feedback comprises continuous tactile feedback of varying pressures.

2. The device of claim 1, wherein said signaling assembly comprises a spring mechanism, wherein said spring mechanism is arranged between said signaling means and said crossbar, and serves to provide continuous contact and limit any impact between the head and signaling means during the use of said device.

* * * * *